(12) United States Patent
Durance et al.

(10) Patent No.: US 10,844,366 B2
(45) Date of Patent: Nov. 24, 2020

(54) APPARATUS AND METHOD FOR DEHYDRATING BIOLOGICAL MATERIALS WITH FREEZING AND MICROWAVING

(71) Applicant: EnWave Corporation, Vancouver (CA)

(72) Inventors: Timothy D. Durance, Vancouver (CA); Jun Fu, Port Coquitlam (CA); Parastoo Yaghmaee, Vancouver (CA); Robert L. Pike, Vancouver (CA)

(73) Assignee: Enwave Corporation, Vancouver (CA)

( * ) Notice: Subject to any disclaimer, the term of this patent is extended or adjusted under 35 U.S.C. 154(b) by 140 days.

(21) Appl. No.: 16/033,767

(22) Filed: Jul. 12, 2018

(65) Prior Publication Data

US 2018/0327737 A1    Nov. 15, 2018

Related U.S. Application Data

(63) Continuation of application No. 13/063,718, filed as application No. PCT/CN2009/001259 on Sep. 11, 2009, now Pat. No. 10,023,857.

(Continued)

(51) Int. Cl.
*F26B 3/34* (2006.01)
*C12N 13/00* (2006.01)
(Continued)

(52) U.S. Cl.
CPC ............... *C12N 13/00* (2013.01); *A23L 3/54* (2013.01); *C12M 47/14* (2013.01); *C12N 1/04* (2013.01);
(Continued)

(58) Field of Classification Search
CPC ...... C12N 13/00; F26B 25/001; F26B 25/003; F26B 25/02; F26B 25/06; F26B 25/063;
(Continued)

(56) References Cited

U.S. PATENT DOCUMENTS 2,512,604 A    6/1950   Bierwirth
4,142,303 A *  3/1979   Fraser ............... F26B 5/06
                                                    34/92

(Continued)

FOREIGN PATENT DOCUMENTS

CN     101126596 A    2/2008
GB        593806     10/1947

(Continued)

OTHER PUBLICATIONS

"The International Search Report and Written Opinion of the International Searching Authority", in connection to PCT/CA2009/001259 filed Sep. 11, 2009 dated Jan. 5, 2010.

*Primary Examiner* — John P McCormack
(74) *Attorney, Agent, or Firm* — McKee, Voorhees & Sease, PLC

(57) ABSTRACT

An apparatus and method for dehydrating biological materials, such as vaccines and microorganism cultures, in which the materials are dehydrated in an evacuated container which is in a microwave waveguide that is open to the atmosphere. The apparatus comprises means for freezing the container of biological material, a microwave generator, a waveguide, means for introducing the container into the waveguide, means for applying a vacuum to the container and means for removing the dehydrated material from the waveguide. In the method of the invention, the container of biological material is put in a microwave waveguide open to the atmosphere, a vacuum is applied to the container, the material is frozen and is radiated to dehydrate it. The dehydrated material is then removed from the waveguide.

7 Claims, 6 Drawing Sheets

Related U.S. Application Data

(60) Provisional application No. 61/096,567, filed on Sep. 12, 2008.

(51) Int. Cl.

| | | |
|---|---|---|
| *A23L 3/54* | (2006.01) | |
| *C12M 1/00* | (2006.01) | |
| *C12N 1/04* | (2006.01) | |
| *C12N 9/96* | (2006.01) | |
| *F26B 5/06* | (2006.01) | |
| *F26B 25/00* | (2006.01) | |

(52) U.S. Cl.
CPC ................. *C12N 9/96* (2013.01); *F26B 5/06* (2013.01); *F26B 25/001* (2013.01)

(58) Field of Classification Search
CPC ........... F26B 5/06; F26B 5/048; C12M 47/14; A23L 3/54
USPC .................................................... 34/263, 259
See application file for complete search history.

(56) References Cited

U.S. PATENT DOCUMENTS

| | | | |
|---|---|---|---|
| 4,616,427 A | 10/1986 | Takeuchi et al. | |
| 4,856,203 A | 8/1989 | Wennerstrum | |
| 5,117,564 A | 6/1992 | Taguchi et al. | |
| 5,129,162 A | 7/1992 | Hemmersbach et al. | |
| 5,211,808 A | 5/1993 | Vilardi et al. | |
| 5,298,707 A | 3/1994 | Sprecher et al. | |
| 5,338,409 A | 8/1994 | Heierli | |
| 5,638,453 A | 6/1997 | McLaughlin | |
| 5,766,520 A | 6/1998 | Bronshtein | |
| 6,225,611 B1 | 5/2001 | Pearcy et al. | |
| 6,627,163 B1 | 9/2003 | Awakowicz et al. | |
| 6,684,524 B1 | 2/2004 | Sennhenn et al. | |
| 6,692,695 B1 | 2/2004 | Bronshtein et al. | |
| 6,848,196 B2 * | 2/2005 | Brulls .................... F26B 5/06 34/268 |
| 6,884,866 B2 | 4/2005 | Bronshtein et al. | |
| 7,007,405 B2 | 3/2006 | Hajek et al. | |
| 8,173,941 B2 * | 5/2012 | Lang .................... H05B 6/806 219/679 |
| 8,793,895 B2 | 8/2014 | Gasteyer, III et al. | |
| 2004/0219687 A1 | 11/2004 | Torii et al. | |
| 2004/0231184 A1 | 11/2004 | Wefers | |
| 2005/0263536 A1 | 12/2005 | Selfridge et al. | |
| 2006/0286234 A1 | 12/2006 | Tsai et al. | |
| 2007/0271811 A1 | 11/2007 | Tsuruta et al. | |
| 2009/0007452 A1 | 1/2009 | Cho | |
| 2010/0012649 A1 | 1/2010 | Cho | |
| 2010/0255195 A1 | 10/2010 | Lambert et al. | |

FOREIGN PATENT DOCUMENTS

| | | |
|---|---|---|
| GB | 608611 | 9/1948 |
| GB | 629979 | 10/1949 |
| WO | 9738585 A1 | 10/1997 |
| WO | 0126815 A1 | 4/2001 |
| WO | 2008025258 A1 | 6/2008 |
| WO | 2008134835 A1 | 11/2008 |
| WO | 2009033285 A1 | 3/2009 |
| WO | 2009049409 A1 | 4/2009 |

\* cited by examiner

APPARATUS AND METHOD FOR DEHYDRATING BIOLOGICAL MATERIALS WITH FREEZING AND MICROWAVING

CROSS-REFERENCE TO RELATED APPLICATIONS

This application is a Continuation Application of U.S. Ser. No. 13/063,718, filed May 6, 2011, which claims priority to PCT/CA2009/001259 filed Sep. 11, 2009, which claims priority under 35 U.S. § 119 to provisional application Ser. No. 61/096,567, filed Sep. 12, 2008, which are herein incorporated by reference in their entirety.

FIELD OF THE INVENTION

The invention pertains to apparatuses and methods for microwave vacuum-drying of biological materials, such as vaccines, antibiotics, antibodies enzymes, proteins and microorganism cultures.

BACKGROUND OF THE INVENTION

Many biologically-active materials, such as vaccines, microbial cultures, etc., are dehydrated for purposes of storage. Methods used in the prior art include freeze-drying and air-drying methods such as spray-drying. Dehydration generally lowers the viability of the materials. Freeze-drying allows higher viability levels than air-drying but it requires long processing times and is expensive. It also causes some level of loss of viability in the dried materials.

It is also known in the art to dehydrate biological and other materials using a resonance chamber type of microwave vacuum dehydrator. This directs microwave energy into a vacuum chamber that serves as a resonance cavity for microwaves. However, particularly where the quantity of material being dried is relatively small, which is commonly the case with biomaterials, controlling the temperature of the material can be difficult. When microwaves are reflected within a resonance chamber, as the material dries the microwave energy output of the apparatus must be absorbed by less and less water and material in the sample. The mass of the material to be processed also has to be matched with the microwave power of the apparatus; quantities of material that are small relative to the microwave power of the apparatus may reach high temperatures when drying because of the abundance of microwave energy absorbed by the material.

SUMMARY OF THE INVENTION

The invention provides an apparatus and method for dehydrating biological materials, in which the materials are dehydrated in an evacuated container which is in a microwave waveguide that is open to the atmosphere. Being open, the waveguide can be air-cooled to avoid overheating of the material. Since the dehydration is done under vacuum, i.e. at a pressure that is less than atmospheric pressure, the boiling point of water is reduced so the evaporation occurs at lower temperatures, minimizing damage to the biological activity of the material being dried. More control of the temperature of the material can be achieved using the invention than using a resonance chamber type of microwave vacuum dehydrator. Very small quantities of material can be processed without overheating.

According to one embodiment of the invention, the apparatus comprises means for freezing a container of biological material, a microwave generator, a waveguide that is open to the atmosphere, means for introducing the container of biological material into the waveguide, means for applying a vacuum to the container, and means for removing the dehydrated material from the waveguide.

The apparatus may optionally include means for effecting relative movement between the sample in the waveguide and the microwave field. This may comprise means for moving the container through the waveguide, or means for moving the generator, or means for moving the biological material within the container. The apparatus may optionally include means for removing a cap from the container, and means for sealing the container.

According to another embodiment of the invention, the apparatus has a waveguide with an input end for the introduction of a microwave-transparent container of a biological material and a discharge end for removal of the container. The apparatus includes means for introducing the container into the input end, means for removing a cap from the container and means for applying a high vacuum (sufficient to cause and/or maintain freezing of the material) to the container. It includes means for moving the evacuated container through the microwave guide from the input end to the discharge end, means for replacing the cap onto the container and means for removing the container from the microwave guide at the discharge end. The apparatus may include a microwave absorbing sink at the end of the waveguide opposite to the generator.

According to another embodiment of the invention, there is provided a method for dehydrating biological materials. A container is provided holding the biological material to be dehydrated, the container being transparent to microwave radiation. The container is put in a microwave waveguide that is open to the atmosphere. A vacuum is applied to the container. The material is frozen, either by the application of the vacuum or before being put into the waveguide. Microwave radiation is applied to dehydrate the biological material. The dehydrated material is removed from the waveguide. Optionally, the container of dehydrated material is sealed before removal from the waveguide or from the vacuum.

Where the container of material is capped before it is put into the microwave guide, the method includes removing the cap before applying microwave radiation. The method may optionally include the step of effecting relative movement between the sample in the waveguide and the microwave field. This may be either the step of moving the evacuated container through the microwave waveguide while applying the microwave radiation, or the step of moving the generator.

The invention accordingly produces containers of dehydrated biological material, having a moisture content as low as, for example, three to four percent or lower. It is particularly suitable for the dehydration of proteins, for example monoclonal antibodies, enzymes and polypeptides.

These and other features of the invention will be apparent from the following description and drawings of the preferred embodiments.

DESCRIPTION OF THE PREFERRED EMBODIMENTS

The Dehydrating Apparatus

Figure 1:
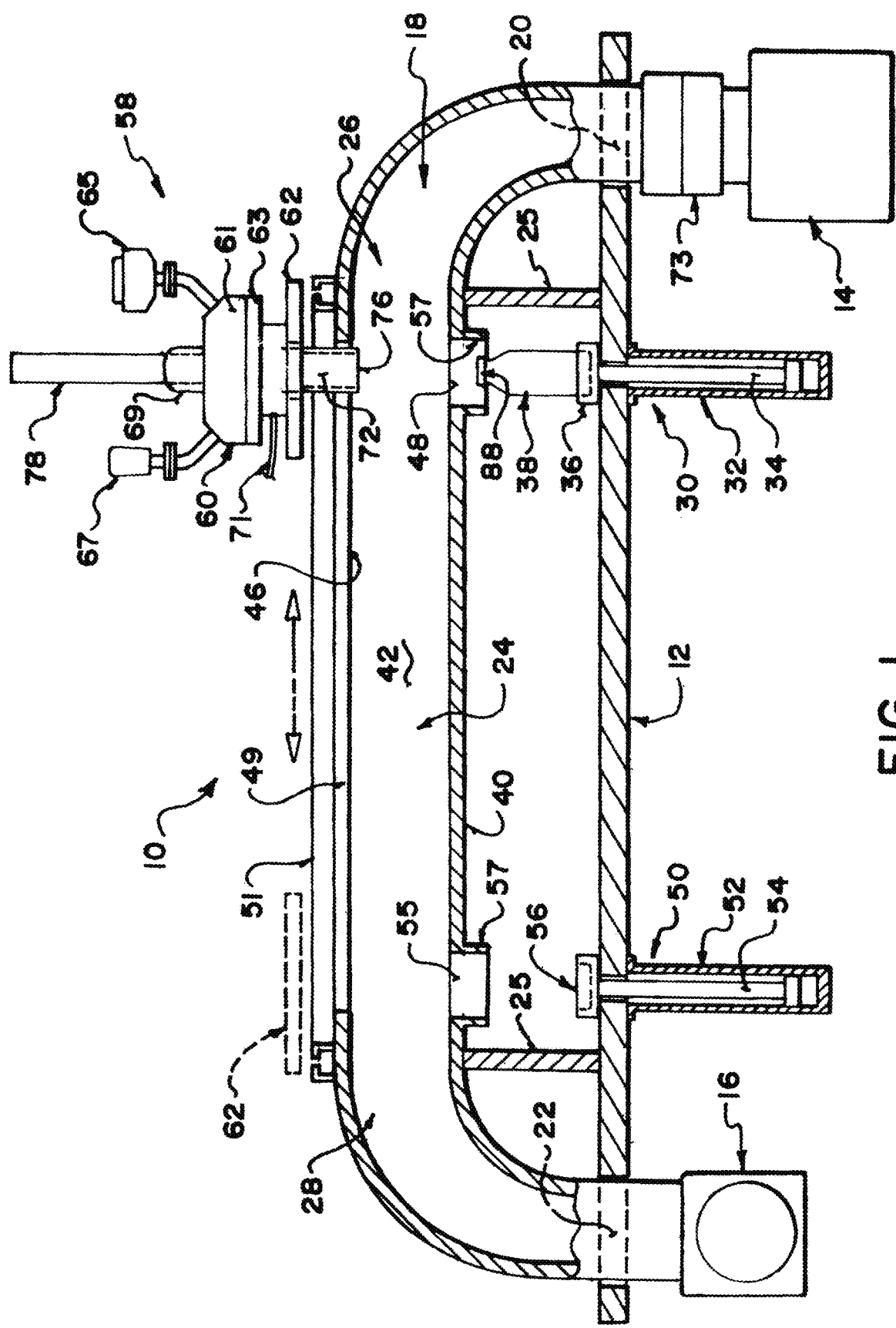
FIG. 1 is a side elevation view, partly in section, of an apparatus according to one embodiment of the invention.

The dehydrating apparatus 10 has a support platform 12 with a microwave generator 14, a circulator 73 and a water sink 16 positioned below the platform 12. A microwave waveguide 18 above the platform extends between the circulator 73, and the water sink 16, passing through spaced-apart bores 20, 22 in the platform 12. The waveguide 18 is supported on the platform 12 by a frame 25. The waveguide 18 includes a longitudinally-extending section, referred to herein as the treatment section 24, through which the material to be dehydrated is moved, as described below.

The treatment section 24 has a bottom wall 40, side walls 42, 44 and an upper wall 46. A longitudinal slot 49 extends through the upper wall 46. The interior of the waveguide 18 is accordingly open to the atmosphere. The opening of the slot 49 is surrounded by a microwave choke 51, for reducing the escape of microwave radiation through the slot. There is a moveable cover (not shown) above the slot and choke to reduce the escape of radiation. The treatment section 24 has a product input end 26, into which the container of material to be dehydrated is introduced, and a product discharge end 28, from which the container of dehydrated material is removed. For purposes of the present description of the preferred embodiment, the container is a microwave-transparent vial 38 for containing, for example, a protein.

A vial-lifting mechanism 30 is affixed to the support platform 12 under the input end 26 of the treatment section 24 of the waveguide. The mechanism comprises an air cylinder 32 with a vial-lifting piston 34, mounted on the underside of the platform 12, with the piston 34 extending through a bore in the platform 12, and a vial-holding platform 36 on the upper end of the piston 34 for holding the vial 38 of material. The treatment section 24 of the waveguide 18 has a port 48 in its bottom wall 40 above the vial-holding platform 34, for entry of the vial 38 and the vial-lifting platform 36 into the treatment section 24.

A vial-lowering mechanism 50 is affixed to the support platform 12 under the product discharge end 28 of the treatment section 24. This mechanism is structurally the same as the vial-lifting mechanism 30, and comprises an air cylinder 52 with a vial-lowering piston 54, extending through a bore in the support platform 12, and a vial-holding platform 56 on the upper end of the piston 54. The treatment section 24 of the waveguide 18 has a port 55 in its bottom wall 40 above the vial-holding platform 56, for removal of the vial from the treatment section 24 after dehydration of the material. A tube 57 extends downwardly around each of the ports 48, 55 to reduce leakage of radiation from the waveguide.

A vial pickup head 58 provides for the transport of the vial 38 through the treatment section 24. The pickup head 58 has a body 60 affixed to a movable support platform 62. The platform 62 is arranged for movement along the treatment section 24 of the waveguide by a pickup head moving mechanism 64. This mechanism comprises a belt drive 66 supported on the frame 25, parallel to the treatment section 24, and driven by a motor 68. The moveable support platform 62 is affixed to the belt drive 66 for movement thereon, such that actuation of the belt drive 66 moves the pickup head 58 along the length of the treatment section 24. The cover for the waveguide slot can be affixed to, or be an extension of, the support platform 62.

Figure 2:
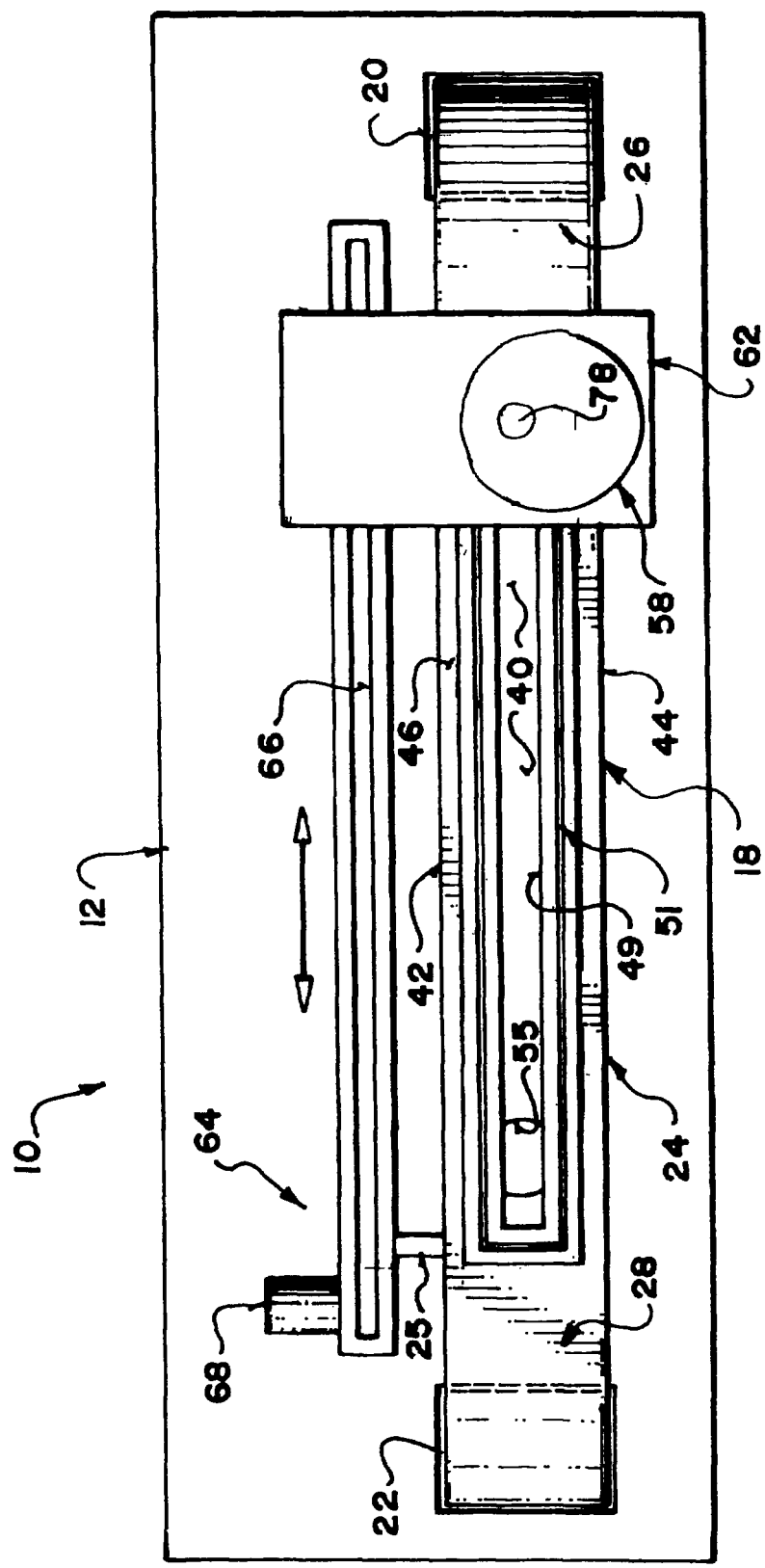
FIG. 2 is a top plan view thereof.
Figure 3:
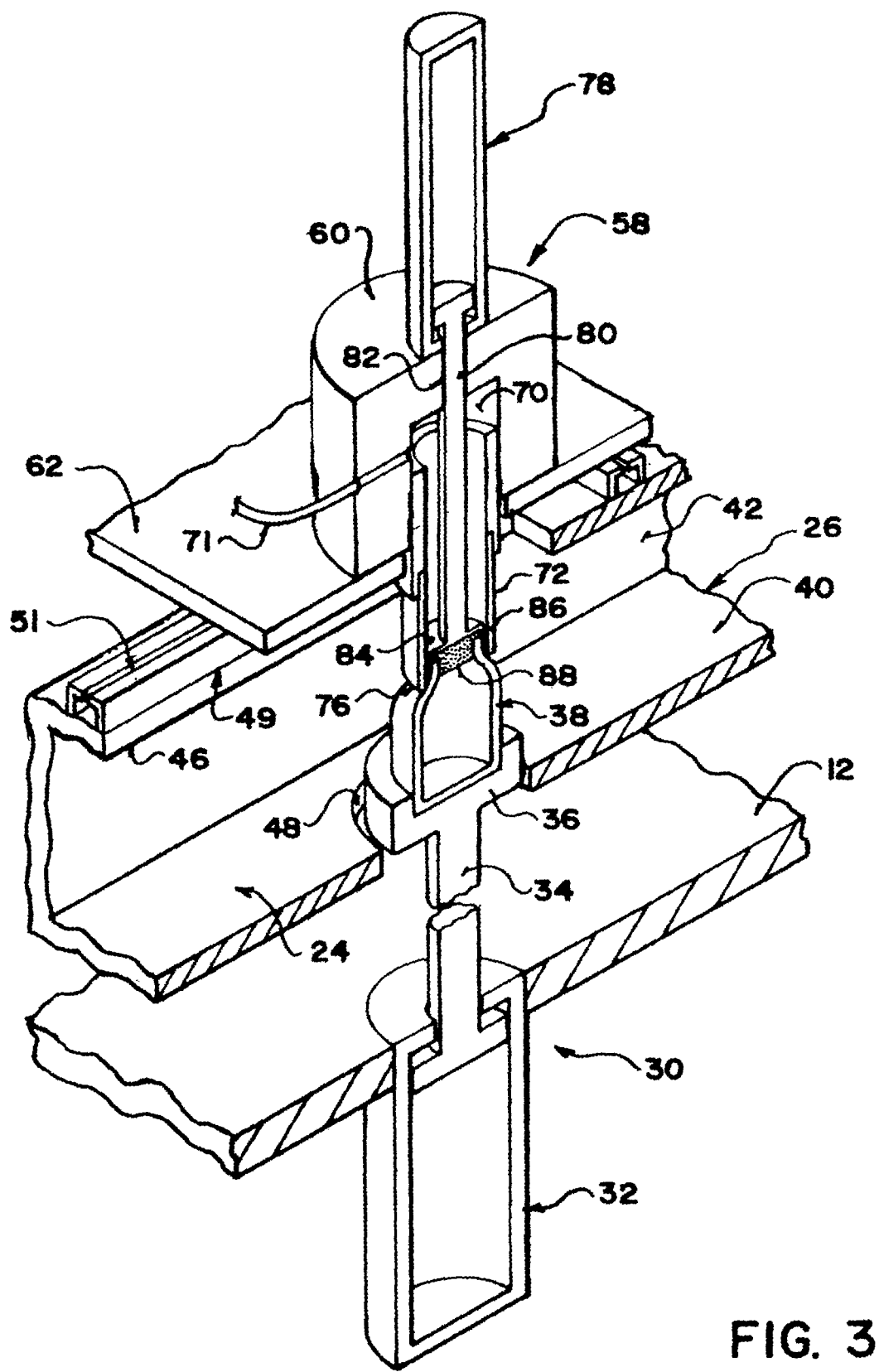
FIG. 3 is a cross-sectional view of part of the apparatus at the input end, prior to removal of the cap from the vial.

The structure of the vial pickup head 58, best seen in FIG. 1, has a body 60 with an upper part 61 and a base part 63. The upper part 61 has ports which lead respectively to a condenser 65, a temperature sensor 67 and a vacuum sensor 69 (omitted from FIGS. 2 to 4 for clarity). The condenser 65 contributes to the condensation of moisture given off from the material during dehydration. The temperature sensor 67 and vacuum sensor 69 respectively measure the temperature and pressure within the vial. The upper part 61 is rotatable on the base part 63 of the pickup head body 60 about a vertical axis, in order to permit the vertical alignment of the respective sensors with the vial, when a measurement is desired.

The body 60 of the pickup head has a vacuum cavity 70 therein in the form of a cylindrical bore. A vacuum source, condenser and vacuum line (not shown) are connected to a vacuum port 71 in the base part 63 of body 60 of the vial pickup head to provide for the evacuation of the vacuum cavity 70 and removal and condensation of moisture from the material. A vial pickup sleeve 72 is mounted in the vacuum cavity 70 with its upper portion in the vacuum cavity 70 and its lower portion extending through a bore in the pickup head support platform 62 and through the longitudinal slot 49 in the upper wall 46. The sleeve 72 thus extends into the treatment section 24 of the waveguide 18. A sealing surface 76 is provided at the bottom edge of the sleeve 72 for airtight sealing engagement with the vial 38.

An air cylinder 78 is affixed to the upper part 61 of the pickup head body 60. It has a piston 80 which extends through a bore 82 in the upper end of the body 60 and into the pickup sleeve 72. A cap holder 84 at the bottom end of the piston 80 has a circumferential flange 86 shaped and adapted to engage and hold a cap 88 of the vial 38.

In order to provide for air-cooling of the vial during the dehydration process, a compressed air line (not shown) may be attached to the pickup head support platform 62, directing compressed air at the vial 38 through the slot 49 in the upper wall 46 of the treatment section. Alternatively, air vanes may be provided on the lower part of the pickup sleeve 72 to blow air in the waveguide against the vial as it is being spun.

For freezing of the biological material prior to microwaving, the vacuum system that is provided is one capable of evacuating the container to a pressure less than about 4 mm of mercury, more accurately 4.58 mm of mercury, the triple point pressure of water. Typically, pressures of about 2.5 mm of mercury or less are required, because solutions of biological materials have a lower freezing point than pure water. Alternatively, a freezer such as a liquid nitrogen bath or low temperature freezer (not shown in the drawings) is provided.

It will be understood that the apparatus 10 also includes appropriate air lines and controls to actuate the air cylinders, a vacuum line and controls to evacuate the vacuum chamber 70, and controls to operate the drive motor.

In an alternative embodiment of the apparatus (not shown in the drawings) the microwave generator is mounted on a moveable stand so it can be moved, relative to the sample, during microwaving. In this case, the sample of material is stationary within the waveguide and relative movement between the sample and the microwave field is achieved by moving the generator rather than the sample. Such relative movement evens out the energy field experienced by the sample.

In another alternative embodiment of the apparatus (not shown in the drawings) the container remains within the waveguide and the biological material is moved through the container. The container is stationary and the material is moved by means such as vibration or gravity.

The Methods of Dehydrating

At the start of a cycle of operation of the dehydrating apparatus 10, the vial-lifting piston 34 and the vial-lowering piston 54 are both in their retracted positions, such that the vial-holding platforms 36, 56 are on the support platform 12. The pickup head piston 80 is also in its retracted position, such that the cap holder 84 is in its raised position within the body 60 of the pickup head 58. The pickup head support platform 62 is at the inlet end 26 of the treatment section 24 of the waveguide 18, with the pickup head 58 vertically aligned with the vial entry port 48. The vial 38 with material to be dehydrated, e.g. a protein, covered by a cap 88 and at atmospheric pressure, is placed on the vial-holding platform 36.

The vial-lifting cylinder 32 is actuated to raise the piston 34 and the vial-holding platform 36, lifting the vial 38 through the vial entry port 48 into the treatment section 24 of the waveguide, until the shoulder of the vial abuts the sealing surface 76 at the lower end of the vial pickup sleeve 72. The pickup head air cylinder 78 is then actuated, to lower the pickup head piston 80 and cap holder 84 to engage the cap 88 of the vial. This position of the apparatus is shown in FIG. 8. A high vacuum is then applied to the vacuum chamber 70 by means of the vacuum source and line, reducing the absolute pressure in the vacuum chamber to less than about 2.5 mm of mercury, alternatively less than about 0.2 mm of mercury.

The pickup head air cylinder 78 is then actuated, lifting the cap holder 84 and removing the cap 88 from the vial 38. This removal is facilitated by the pressure differential between the inside of the vial, which is at atmospheric pressure, and the partial vacuum of the vacuum chamber 70 and pickup sleeve 72. The cap removal causes a vacuum to be applied to the vial 38. The vacuum applied through the pickup sleeve 72 causes a seal between the vial and the pickup sleeve 72 at the sealing surface 76, permitting the vial to be held securely by the pickup sleeve 72. The vial-lifting cylinder 32 is then actuated to lower the vial-lifting piston 34, withdrawing the vial-holding platform 36 from the waveguide 18.

The application of high vacuum to the container cools the sample below its freezing point.

The microwave generator 14 is then actuated, causing microwave energy to travel through the waveguide 18 to the water sink 16. The circulator 73 prevents microwave energy from re-entering the generator. The belt drive motor 68 is actuated, to move the belt drive 66 and accordingly the pickup head support platform 62. The direction of movement of the support platform 62 is towards the discharge end 28 of the treatment section 24. The vial 38 remains evacuated. The heating of the biological material by the microwave energy causes dehydration of the material. If desired, the pressure and temperature in the vial can be measured during the dehydration process by means of the sensors 69, 67. The dehydration of the sample is by sublimation, as the ice turns directly to gas.

Figure 4:
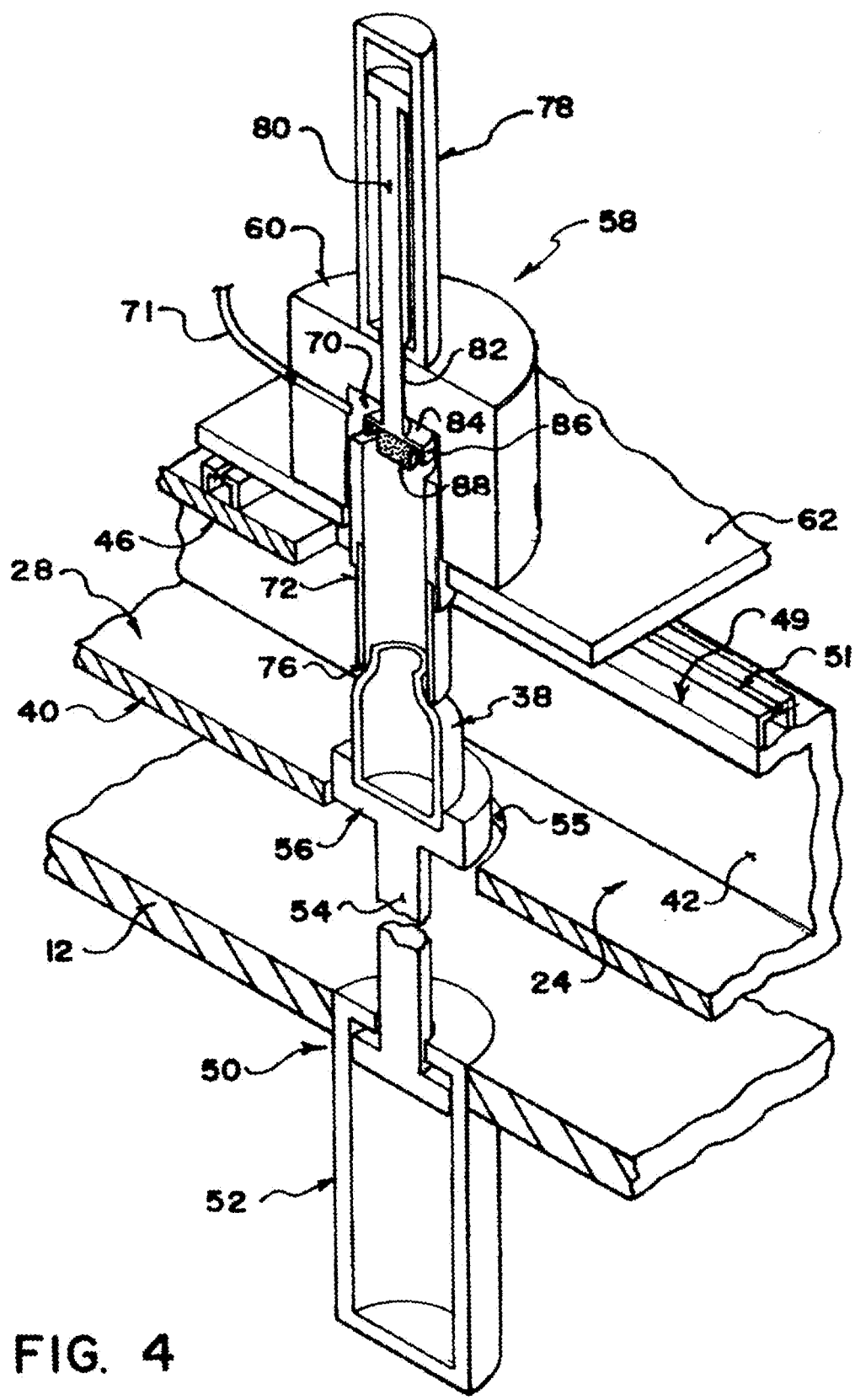
FIG. 4 is a cross-sectional view of part of the apparatus at the discharge end, prior to replacement of the cap on the vial.

At the discharge end 28, the vial 38 is brought into alignment with the vial removal port 55 in the bottom wall 40 of the treatment section 24 and the belt drive motor 68 is stopped. The microwave generator 14 is deactivated. The air cylinder 52 is actuated to raise the vial-lowering piston 54, extending the vial-holding platform 56 through the port 55 into the treatment section 24 of the microwave guide so it engages the bottom of the vial 38. This position is shown in FIG. 4. The pickup head air cylinder 78 is actuated to lower the pickup head piston 80, pushing the cap 88 back onto the vial 38. The vacuum in the vacuum chamber 70 is then released. This breaks the seal between the pickup sleeve 72 and the vial 38 at the sealing surface 76, releasing the vial from the grip of the sleeve. The release of vacuum also results in a pressure differential between the inside of the vial, which is at reduced pressure, and the vacuum chamber 70 and pickup sleeve 72, which are now at atmospheric pressure. The pickup head air cylinder 78 is then actuated, to lift the piston 80 and the cap holder 84. Due to the pressure differential, the reduced pressure in the vial holds the cap 88 in place on the vial 38 as the cap holder 84 is retracted. The air cylinder 52 is then actuated to lower the vial-holding platform 56, and with it the vial 38, withdrawing the vial from the waveguide 18. The vial can then be manually removed from the apparatus 10. It is a vacuum sealed, capped vial containing dehydrated material.

To return the apparatus to the starting condition for processing of a further vial of material, the drive motor 68 is actuated to return the pickup head 58 to the input end 26 of the treatment section 24.

Figure 5:
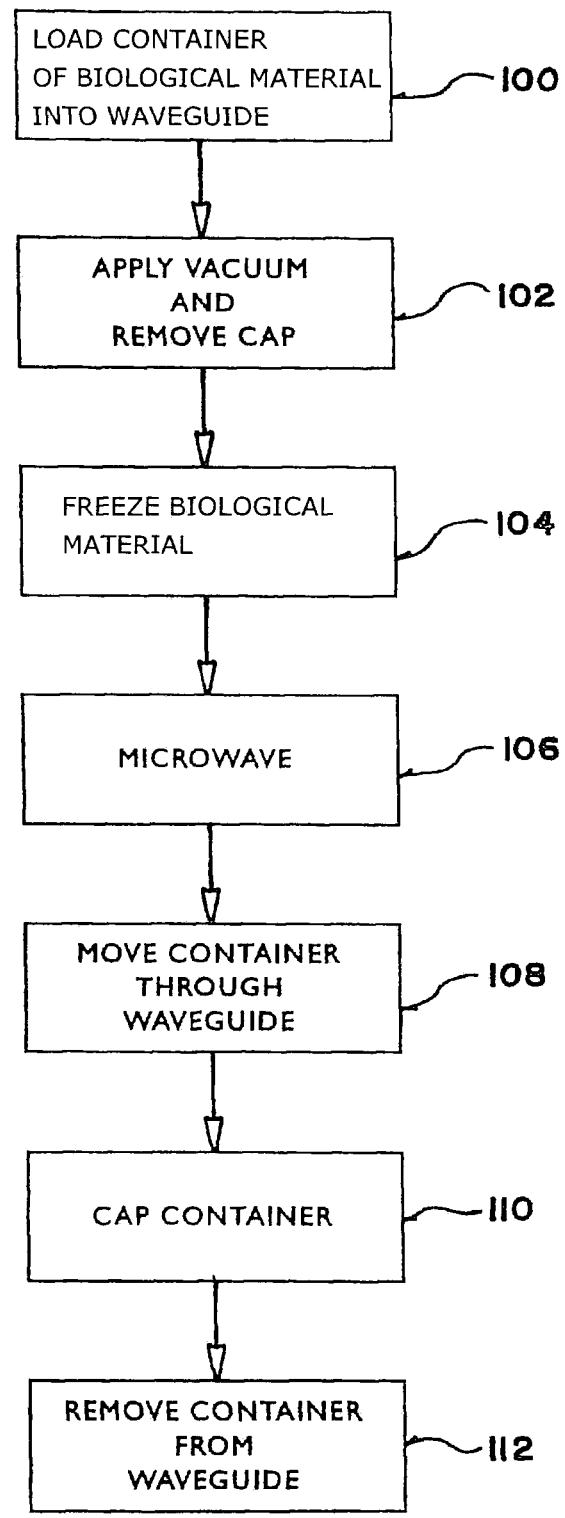
FIGS. 5 and 6 are flow diagrams of methods of dehydration according to the invention.

The foregoing method can be understood in general terms as comprising the following steps, as illustrated in the flow diagram of FIG. 5. In step 100, the capped container of biological material is loaded into the waveguide. In step 102, the cap is removed and a high vacuum is applied to the container, causing freezing of the material in step 104. In step 106, microwave energy is directed through the waveguide. In step 108, the container is moved through the waveguide to the outlet end. In step 110, the container is capped. In step 112 the evacuated container of dehydrated material is removed from the waveguide.

Instead of capping the container of dehydrated material in the waveguide, the container may alternatively be removed uncapped. Capping would then be done subsequently, after removal of the container from the apparatus.

Figure 6:
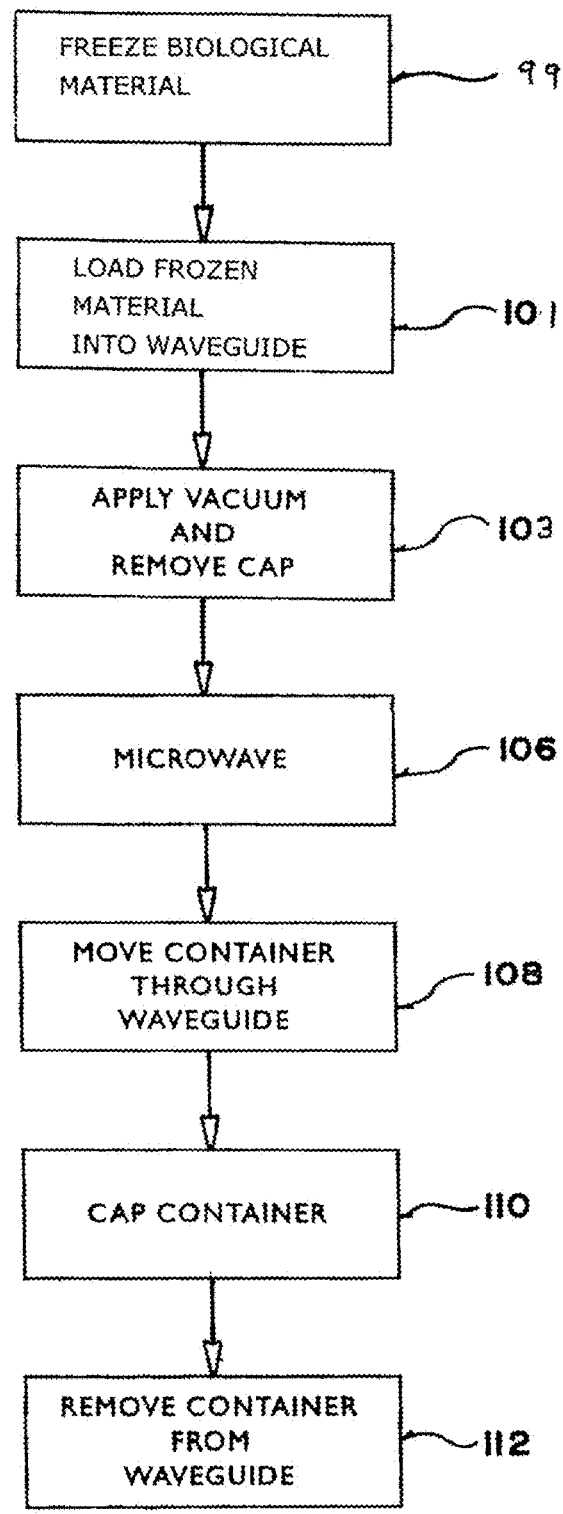

Alternatively, the container of material is frozen before processing, for example by placing it in a bath of liquid nitrogen or low temperature freezer. The frozen material is then processed in the dehydrating apparatus 10. The step of freezing in this method is thus a preliminary step before dehydrating the biological material in the apparatus. This method is illustrated in the flow diagram of FIG. 6. In step 99, the container of material is frozen in liquid nitrogen. The frozen material is then loaded into the waveguide in step 101. In step 103, the cap is removed and a vacuum is applied, typically less than 2.5 mm of mercury. This low pressure keeps the material frozen during microwaving. The material is then processed with steps 106, 108, 110 and 112.

Alternatively, the vial may be kept stationary while the microwave field is moved about it, for example by moving the microwave generator relative to the sample.

Dehydration of biological materials can also be achieved without the step of moving the container through the waveguide, or moving the generator. Movement equalizes the field to which the material is exposed. Without such movement, it is necessary that the intensity of microwave energy at the fixed position of the container in the waveguide be appropriate for the sample. The steps of this method can comprise the steps illustrated in the flow charts of FIG. 5 or 6, omitting step 108 of moving the container.

Example 1

An apparatus according to the invention has a microwave generator having a power output of 900 watts, a water sink and a microwave guide extending between them. The guide has a treatment section approximately 33 cm long, with a channel that is rectangular in cross-section approximately 5.25 cm high and 10.9 cm wide. The slot in the upper wall of the treatment section is approximately 2.8 cm wide and is surrounded by a microwave choke.

Example 2

*Lactobacillus salivarius* stationary phase cells were mixed with 10% skim milk powder and divided into aliquots of 0.5 ml and were frozen at −80° C. freezer for one day and then dried in accordance with the invention (100-700 W, 19-21 minutes, vacuum of 2 mm mercury). The final viable cells were counted by plating dilutions series on petrifilm after 48 hours anaerobic incubation at 37° C. The percent of colony-forming units that survived dehydration were 52.2±9.67%. The moisture content of the dehydrated material was 3.48±1.23%.

Example 3

A 10% lysozyme solution was prepared using powder enzyme and sterile distilled water. An aliquot of 0.5 ml of 10% enzyme was poured into a container and was frozen at −80° C. for two hours. Frozen samples were dried in accordance with the invention (800 W, vacuum 2 mm mercury, 27 minutes dehydration time). The activity of enzyme before and after drying was measured using Shugar method.

| Activity and moisture of 10% lysozyme before and after dehydration | | |
| --- | --- | --- |
| Enzyme activity Shugar unit/mg | | |
| Before Treatment | After Treatment | Final Moisture Content |
|  | 14133 ± 2584 | 2-5% |

Although the invention has been described in terms of various embodiments, it is not intended that the invention be limited to these embodiments. Various modifications within the scope of the invention will be apparent to those skilled in the art.

LIST OF COMPONENTS IN THE DRAWINGS 10 dehydrating apparatus
12 support platform
14 microwave generator
16 water sink
18 microwave waveguide
20, 22 bores in platform 12 for the waveguide
24 treatment section of the waveguide
25 frame
26 input end of treatment section
28 discharge end of treatment section
30 vial-lifting mechanism
32 vial-lifting air cylinder
34 vial-lifting piston
36 vial-holding platform
38 vial
40 bottom wall of treatment section
42, 44 side walls of treatment section
46 upper wall of treatment section
48 vial entry port
49 longitudinal slot in upper wall of treatment section
50 vial-lowering mechanism
51 microwave choke
52 vial-lowering air cylinder
54 vial-lowering piston
55 vial-removal port
56 vial-holding platform
57 tubes below vial ports
58 vial-pickup head
60 body of vial-pickup head
61 swivelling part of 60
62 pickup head support platform
63 base part of 60
64 pickup head moving mechanism
65 condenser
66 belt drive
67 temperature sensor
68 belt drive motor
69 vacuum sensor
70 vacuum cavity in vial-pickup head
71 vacuum port in body 60
72 vial-pickup sleeve
73 circulator
76 sealing surface of pickup sleeve
78 air cylinder on pickup head
80 piston for air cylinder on pickup head
82 bore in top of body 60
84 cap holder
86 flange on cap holder
88 cap of vial

The invention claimed is:

1. An apparatus for dehydrating a biological material, comprising:
    (a) a microwave generator;
    (b) a waveguide to direct microwave radiation from the generator, the waveguide being open to the atmosphere;
    (c) a container-lifting mechanism for introducing a microwave-transparent container of the material into the waveguide;
    (d) a vacuum source for applying a vacuum to the container sufficient to cause or maintain freezing of the material; and
    (e) a container-lowering mechanism for removing the container from the waveguide.

2. An apparatus for dehydrating a biological material, comprising:
    (a) a microwave generator;
    (b) a waveguide to direct microwave radiation from the generator, the waveguide being open to the atmosphere;
    (c) a microwave-transparent container in the waveguide for holding the material;
    (d) a vacuum source for applying a vacuum to the container sufficient to cause or maintain freezing of the material; and
    (e) a container-removing mechanism for removing the container from the waveguide.

3. An apparatus for dehydrating a biological material, comprising:
    (a) a microwave generator;
    (b) a waveguide to direct microwave radiation from the generator, the waveguide being open to the atmosphere;
    (c) means for introducing a microwave-transparent container of the material into the waveguide;

(d) means for applying a vacuum to the container sufficient to cause or maintain freezing of the material; and (e) means for removing the material from the waveguide.

4. An apparatus for dehydrating a biological material, comprising:

(b) a microwave generator;

(b) a waveguide to direct microwave radiation from the generator, the waveguide being open to the atmosphere;

(c) a microwave-transparent container in the waveguide for holding the material;

(d) means for applying a vacuum to the container sufficient to cause or maintain freezing of the material; and (e) means for removing the material from the waveguide.

5. A method for dehydrating a biological material, comprising the steps of:

(a) providing a microwave-transparent container holding the biological material to be dehydrated;

(b) putting the container in a microwave waveguide that is open to the atmosphere;

(c) applying a vacuum to the container in the waveguide;

(d) freezing the material;

(e) applying microwave radiation to dehydrate the material in the container by sublimation; and (f) removing the dehydrated material from the waveguide.

6. The method according to claim 5, wherein the freezing of the material is done by the applying of the vacuum to the container.

7. A method for dehydrating a biological material, comprising the steps of:

(a) providing a microwave-transparent container holding the material to be dehydrated;

(b) freezing the material;

(c) putting the container of frozen material into a microwave waveguide that is open to the atmosphere;

(d) applying a vacuum to the container in the waveguide;

(e) applying microwave radiation to dehydrate the material in the container by sublimation; and (f) removing the dehydrated material from the waveguide.

* * * * *

UNITED STATES PATENT AND TRADEMARK OFFICE
CERTIFICATE OF CORRECTION

PATENT NO. : 10,844,366 B2
APPLICATION NO. : 16/033767
DATED : November 24, 2020
INVENTOR(S) : Timothy D. Durance et al.

Page 1 of 1

It is certified that error appears in the above-identified patent and that said Letters Patent is hereby corrected as shown below:

On the Title Page

Column 1, (63) Related U.S. Application Data:
DELETE "PCT/CN2009/001259" before "on"
INSERT --PCT/CA2009/001259-- before "on"

Signed and Sealed this
Thirtieth Day of March, 2021

Drew Hirshfeld
*Performing the Functions and Duties of the
Under Secretary of Commerce for Intellectual Property and
Director of the United States Patent and Trademark Office*